US00PP13916P39

(12) United States Plant Patent
Huber

(10) Patent No.: US PP13,916 P3
(45) Date of Patent: Jun. 24, 2003

(54) SPIRAEA PLANT NAMED 'FLOWERING CHOICE'

(75) Inventor: Tony Huber, Laval (CA)

(73) Assignee: Bailey Nurseries, Inc., St. Paul, MN (US)

( * ) Notice: Subject to any disclaimer, the term of this patent is extended or adjusted under 35 U.S.C. 154(b) by 43 days.

(21) Appl. No.: 09/881,811

(22) Filed: Jun. 18, 2001

(65) Prior Publication Data

US 2002/0194657 P1 Dec. 19, 2002

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, GTI JOUVE Retrieval Software, 2002/05, citation(s) for 'Flowering Choice'.*

Canadian Food Inspection Agency, http://www.insptection.gc.ca , Plant Breeder's Right for 'Flowering Choice'.*

Tebbitt, Mark C. International Registration of Cultivar Names for Unassigned Woody Genera 1999 HortScience vol. 35(4), Jul. 2000.*

* cited by examiner

*Primary Examiner*—Bruce R. Campell
*Assistant Examiner*—W C Haas
(74) *Attorney, Agent, or Firm*—Burns, Doane, Swecker & Mathis, L.L.P.

(57) ABSTRACT

A new variety of *Spiraea×Bumalda* plant is provided that is well suited for growing as attractive ornamentation. The new variety is dwarf in nature and exhibits a small compact and rounded growth habit. Large purplish-pink blooms are formed over an extended period of time. The foliage is fine-textured and changes from medium green to orange in the fall. The available Spirea choices are expanded.

2 Drawing Sheets

BOTANICAL/COMMERCIAL CLASSIFICATION

*Spiraea×Bumalda* / Spirea Plant.

VARIETAL DENOMINATION cv. 'Flowering Choice'.

SUMMARY OF THE INVENTION

The new *Spiraea×Bumalda* Burv. plant of the present invention was the product of a controlled breeding program that began in 1976 at Boisbriand, Quebec, Canada. Initially, *Spiraea×Bumalda* 'Goldflame', non-patented in the United States) was crossed with *Spiraea japonica nana 'W. H. Perron Select' (non-patented in the United States). The* $F_1$ seeds were sown in the greenhouse and 403 seedlings were planted and observed in the field. From 1978 to 1988, twenty-seven clones were selected for their yellow foliage. A yellow foliage clone 'SX-1-31-02' was open pollinated and the resulting $F_2$ seed produced 60 percent seedlings having green foliage and 40 percent seedlings having yellow foliage. One of the yellow foliage clones was selected and was open pollinated with the resulting seedlings having 65 percent yellow foliage and 35 percent green foliage. Of these seedlings, one selection was named 'G-DW-80-106' (non-patented in the United States), and served as the female parent of the cross that yielded the new variety of the present invention. The male parent in such cross was *Spiraea japonica,* 'Shirobana' (non-patented in the United States). A single plant of the new variety of the present invention was first observed in 1985 and was selected during 1986 from among the resulting seedlings and has been carefully preserved.

It was found that the new variety of the present invention displays the following combination of characteristics:

(a) Exhibits a small compact and rounded growth habit,
(b) Forms attractive large purplish-pink blooms over an extended period of time, and
(c) Forms fine-textured lanceolate medium green leaves that assume a purplish-red coloration in the fall.

The new variety of the present invention well meets the needs of the horticultural industry and can be grown as distinctive ornamentation. Attractive perfect (bisexual) flowers are produced as compound corymbs after the emergence of the leaves on the current season's wood.

The plants of the new variety can be readily distinguished from those of the 'Little Princess' variety (non-patented in the United States). More specifically, the new variety is a smaller plant, the new variety commonly blooms up to approximately fifteen weeks compared to approximately five weeks for the 'Little Princess' variety, the 'Little Princess' commonly initiates blooming on an earlier date, the blooms of the new variety are larger, the florets of 'Little Princess' are lighter in coloration when they first open and fade to a lighter pink, the leaves of the new variety turn purplish-red in the fall whereas those of the 'Little Princess' variety turn orange, the growth habit is rounded compared to flat-top-rounded for the 'Little Princess' variety, and the new variety produces no follicle whereas the 'Little Princess' variety produces a medium brown follicle.

The new variety of the present invention can be distinguished from its 'Shirobana' parent by its shorter and more compact growth habit, longer period of blooming, and the formation of all purplish-pink flowers whereas the flowers of 'Shirobana' are white and pink.

The rooting of cuttings has been used to asexually propagate the new variety at Quebec, Canada. Such propagation can be readily carried out in early spring while using tender cuttings. It has been found that the distinctive combination of characteristics of the new variety is firmly fixed and is reliably transmitted to succeeding generations.

The new variety has been named 'Flowering Choice'.

BRIEF DESCRIPTION OF THE PHOTOGRAPHS

The accompanying photographs show specimens of the new variety in color as nearly true as it is reasonably possible to make the same in color illustrations of this nature. The plants had been propagated from rooted cuttings, were approximately two years of age, and were being grown outdoors during the summer in containers at Quebec, Canada.

DETAILED DESCRIPTION

Figure 1:
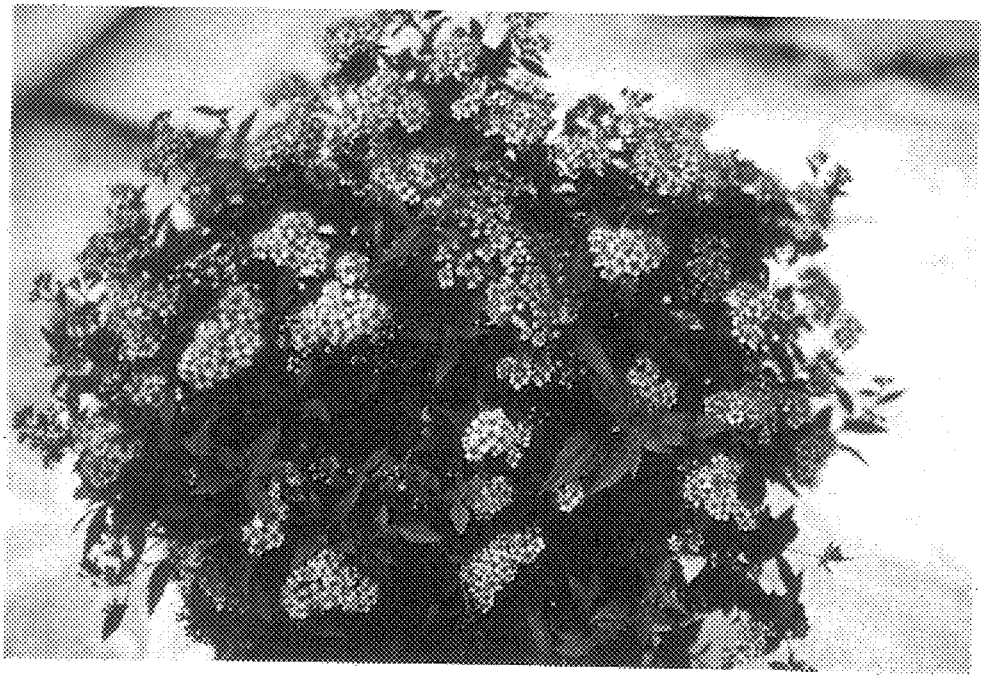
FIG. 1 illustrates an overall view of a typical plant of the new variety while blooming. The attractive small compact rounded growth habit and profusion of blooms are shown.
Figure 2:
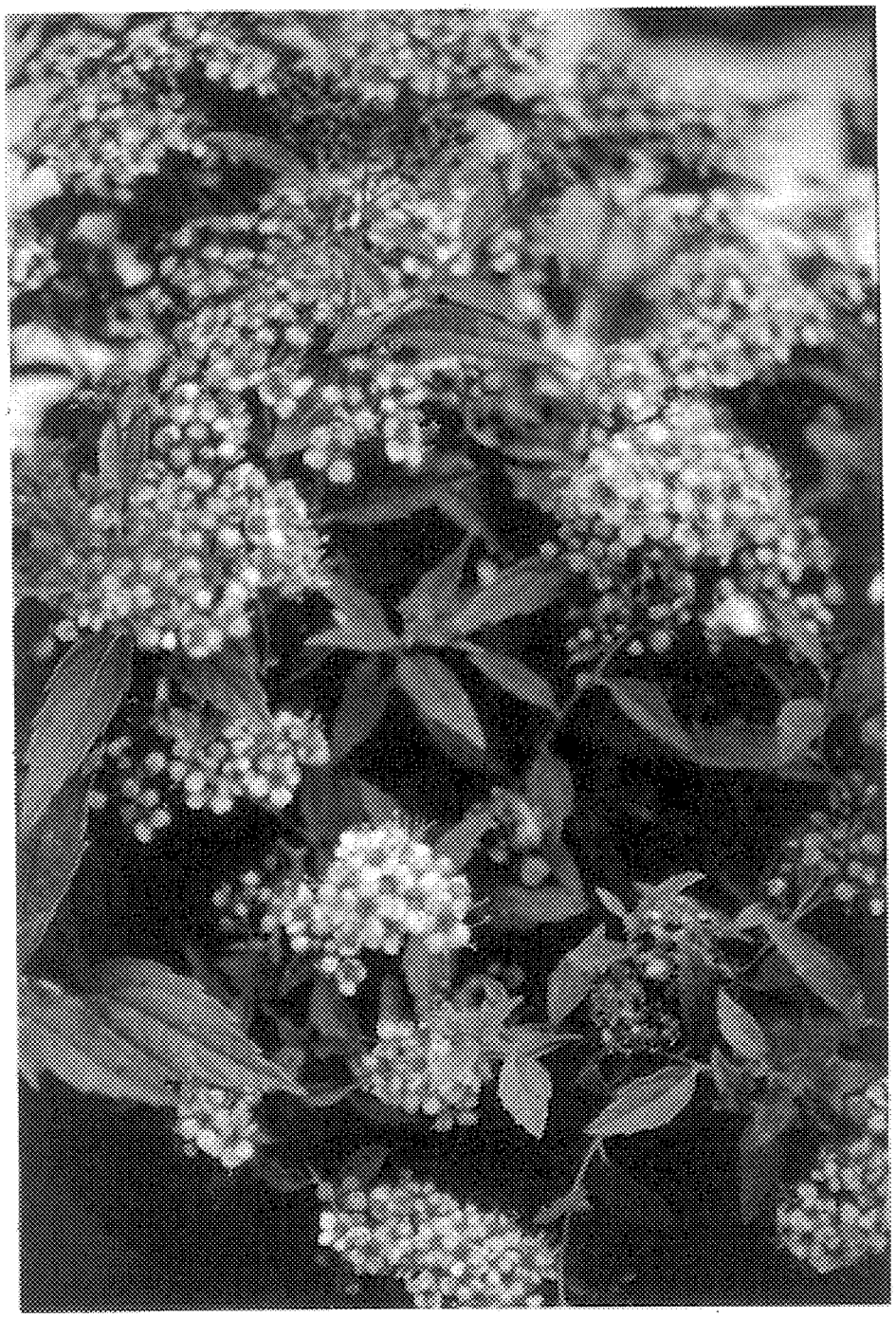
FIG. 2 illustrates a closer view of the foliage and blossoms of the new variety. The attractive purplish-pink flowers and fine-textured foliage are shown.

The following is a detailed description of the new variety that was obtained while observing plants of approximately two years of age during the summer while being grown outdoors in containers at Quebec, Canada. The chart used in the identification of color is The R.H.S. Colour Chart of The Royal Horticultural Society, London, England. Common color terms are to be accorded their customary dictionary significance.

Botanical classification: *Spiraea×Bumalda,* cv. 'Flowering Choice'.

*Female parent.*—*Spiraea×Bumalda,* cv. 'G-DW-80-106'.

*Male parent.*—*Spiraea japonica,* cv. 'Shirobana'.

Plant:

*Type.*—Perennial shrub.

*Growth habit.*—Compact, small, and rounded with a weak tendency to sucker.

*Growth rate.*—Rapid with excellent vigor.

*Height.*—Approximately 27 cm at two years of age. When fully mature assumes a height of approximately 35 to 40 cm.

*Width.*—Approximately 34 cm at two years of age.

*Branching habit.*—Moderately dense.

*Stem cross-section.*—Round.

*Stem surface.*—Smooth.

*Stem shape.*—Straight when viewed from the side.

*Stem diameter.*—Medium.

*Stem color.*—Light brown (Greyed-Orange Group 166A).

*Stem pubescence.*—Absent.

*Secondary shoots.*—Present.

*Tertiary shoots.*—Absent.

*Roots*—Fine fibrous with much branching.

Leaflets:

*Arrangement.*—Alternate.

*Configuration.*—Lanceolate.

*Tip.*—Acute.

*Base.*—Cuneate. This compares to an acute base for the 'Little Princess' variety.

*Length.*—Approximately 3.5 cm.

*Width.*—Approximately 1.3 cm.

*Texture.*—Smooth.

*Pubescence.*—Generally absent with weak pubescence at the margin.

*Margin.*—Serrate with teeth distributed only over the final approximately ⅔s of the blade. This can be compared to the 'Little Princess' variety that has teeth distributed over the complete leaf margin.

*Venation.*—Pinnate, and glabrous with no glaucosity on both surfaces.

*Color.*—Young foliage: Purplish-red when unfolding then when open Yellow-Green Group 144A on the upper surface and Yellow-Green Group 144B on the under surface. Mature foliage: Medium green, Green Group 137B on the upper surface and Green Group 137C on the under surface. Fall foliage: Purplish-red (Greyed-Purple Group 183C to Greyed-Purple Group 187B). This can be compared to orange for the 'Little Princess' variety. Such coloration is influenced by the weather conditions that are encountered.

*Petioles.*—Present, and Yellow-Green Group on young foliage and Green Group 137D on the mature foliage.

Inflorescence:

*Arrangement.*—Compound corymbs after emergence of the leaves.

*Bud shape.*—Short, narrow and round. This compares to a medium length bud for the 'Little Princess' variety.

*Bud color.*—Red-Purple Group 61B.

*Flower size.*—Large, approximately 6.9 cm in diameter. This can be compared to the diameter of approximately 5 cm for the 'Little Princess' variety.

*Type.*—Perfect (bisexual).

*Habit.*—Blooms continuously from late spring to late summer over a period of up to approximately 15 weeks. This can be compared to the 'Little Princess' variety which commonly initiates blooming in mid-spring and blooms for only approximately 5 weeks. Flowering is located on terminal and axillary stems.

*Petal number.*—Five and non-fused.

*Petal texture.*—Smooth.

*Pet shape.*—Substantially round.

*Petal tip.*—Rounded.

*Petal margin.*—Entire.

*Petal color.*—Red-Purple Group 70D with a darker center of Red-Purple Group 71B. This can be compared to a lighter Red-Purple Group 65D with a center of Red-Purple 61B for the 'Little Princess' variety. The coloration lightens somewhat after a few days. For instance, the present variety commonly lightens to Red-Purple Group 65D and the 'Little Princess' variety commonly lightens to Red Group 56D.

*Sepals.*—Five in number with weak pubescence.

*Stamens.*—Located above the petals with distinct carpel formation.

*Follicle.*—None formed. In contrast, the 'Little Princess' variety produces a medium brown follicle.

*Peduncle.*—Present with very weak or no pubescence.

Development:

*Propagation.*—Propagates well using tender cuttings during early spring. Roots commonly are initiated in approximately 21 to 28 days at 20° C. Rooted liners commonly are produced in approximately 5 to 8 weeks in the summer. A plant rooted in June is ready for sale the following Spring.

*Disease resistance.*—Typical of Spirea with no disease sensitivity noted to date. More specifically, no mildew or rust disease problem has been encountered during observations to date.

I claim:

1. A new and distinct variety of Spirea plant that displays the following combination of characteristics:

(a) Exhibits a small compact and rounded growth habit, (b) Forms attractive large purplish-pink blooms over an extended period of time, and (c) Forms fine-textured lanceolate medium green leaves that assume a purplish-red coloration in the fall;

substantially as illustrated and described.

* * * * *